US005698423A

United States Patent [19]
Holowach-Keller et al.

[11] Patent Number: 5,698,423
[45] Date of Patent: Dec. 16, 1997

[54] **METHOD FOR PRODUCING AZADIRACHTIN BY CELL CULTURE OF *AZADIRACHTA INDICA***

[75] Inventors: Lorraine Pierce Holowach-Keller, Lansdale, Pa.; Irina Birman, Ithaca, N.Y.; Dennis Ray Patterson, North Wales, Pa.

[73] Assignee: Rohm and Haas Company, Phila., Pa.

[21] Appl. No.: 473,410

[22] Filed: Jun. 7, 1995

Related U.S. Application Data

[63] Continuation of Ser. No. 156,960, Nov. 22, 1993, abandoned, which is a continuation-in-part of Ser. No. 995,866, Dec. 23, 1992, abandoned.

[51] Int. Cl.$^6$ ..................................................... C12P 17/18
[52] U.S. Cl. ............... 435/119; 435/240.46; 435/240.48; 435/244; 435/172.1; 435/172.3
[58] Field of Search ........................ 435/119, 240.46, 435/240.48, 244, 172.1, 172.3

[56] References Cited

U.S. PATENT DOCUMENTS 2,747,334  6/1956  Routien et al. .
5,153,130  10/1992  Kinnersley et al. .
5,281,618  1/1994  Walter .
5,420,318  5/1995  Lidert ........................................ 554/193
5,552,307  9/1996  Kessler ...................................... 435/171

OTHER PUBLICATIONS

Current Science, vol. 63, No. 3 (1992), pp. 117–122.
Current Science, vol. 58. No. 4 (1989), pp. 184–187 (Naina et al).
Plant Cell Reports, 9:121–124 (1990).
Plant Cell Reports, 9:579–581 (1991).
Plant Cell Reports, 6:449–453 (1987).
Plant Cell Reports, 7:51–54 (1988).
Schmutterer & Ascher Natural Pesticides, from the Neem Tree, pp. 539–541 (1984).
Current Science, vol. 57, No. 1, 1988.
Current Science, vol. 58, No. 4, 1989.
Budavari, The Merck Index, pp. 142–143 (1989).

*Primary Examiner*—Irene Marx
*Attorney, Agent, or Firm*—Thomas D. Rogerson

[57] ABSTRACT

A plant cell suspension culture to derive azadirachtin-producing cells is described. The culture overcomes the disadvantages of the present processes of seed extraction. The culture allows for the continuous production of azadirachtin that is free of pathogens and toxins, independent of environmental conditions. It yields a predictable quantity and quality of bioactive product and permits continuous production at a desired, contained location.

5 Claims, No Drawings

METHOD FOR PRODUCING AZADIRACHTIN BY CELL CULTURE OF *AZADIRACHTA INDICA*

This application is a continuation of Ser. No. 08/156,960, now abandoned, filed Nov. 22, 1993 which was a continuation-in-part of Ser. No. 07/995,866, now abandoned, filed Dec. 23, 1992.

FIELD OF THE INVENTION

The present invention relates to a phytohormone-independent cell culture. In particular, the present invention relates to the use of plant cell cultures for the production of bioactive compounds. In particular, the present invention relates to plant cell cultures that produce the insecticidal tetranortriterpeniod azadirachtin, and processes for obtaining azadirachtin from such cell cultures.

BACKGROUND OF THE INVENTION

Industrial-scale quantities of bioactive compounds may be produced by growing cultured cells in bioreactors of up to 100,000 liters (Payne, et al. (1992) *Plant Cell Culture and Tissue Culture in Liquid Systems*, Oxford University Press, New York; Scragg A. H. (1990); Fermentation systems for plant cells IN: Charlwood, B. V. and M. J. C. Rhodes, Eds *Secondary Products from Plant Tissue Culture*, Oxford University Press, New York). Few commerical-scale examples of plant cell culture of secondary metabolites exist. This is because plant cell culture is generally a more expensive route to desired compounds than is extraction of plant parts harvested from nature. The costs of plant cell culture presently exceed the costs of bacterial and yeast fermentation.

U.S. Pat. No. 4,717,664 (Method of Producing Secondary Metabolites of Plants issued Jan. 5, 1988) discloses a two-stage process for obtaining secondary metabolites from suspension cultures of certain families of plants. In order to maximize the production of desired secondary metabolites, at least two stages of liquid media are used, a growth medium and a production medium. At least one of the components of the production medium is substantially changed from the growth medium.

*Agrobacterium tumefaciens* is a plant pathogenic bacterium that mediates the transfer of genetic material into the chromosomal DNA of suseptible plant cells by a process known as transformation. Transformation alters plant secondary metabolism by the introduction of genes coding for phytohormones into plant chromosomal DNA. As a result, these tumorous cells are able to grow in culture in the absence of exogenously added phytohormones.

Zambryski, et al. ((1989) Cell 56:193–202) describe the sequence of molecular genetic events that occur when Agrobacterium infects susceptible plant cells. The authors further disclose genetic modifications occurring to plant chromosomal DNA, and characteristics of the tumorous growth of transformed plant cells. Saito, et al. ((1992) J. Nat Prod (LLoydia) 55(149–162)) discuss Agrobacterium-mediated gene transfer as a strategy to enhance secondary metabolite production in transgenic medicinal plants. Saito, et al. disclose that suspension cells derived from crown gall tumors have been used for production of some specific secondary metabolites, specifically quinoline alkaloids and isoflavonoid glucosides. Berlin, et al., (1989; *Planta Medica*, 55:685) disclose the use of *Agrobacterium tumefaciens* transformation of Lupinus cell cultures to alter secondary metabolite pathways and made quantitative comparisons between productivity of normal and transformed cultures. Berlin, et al., disclose that nontransformed and transformed suspension cultures produced the same spectrum of compounds, and that transformed cells produced up to ten times more isoflavonoid diglucosides than nontransformed lines. However, the authors also disclose elevated yields of isoflavones in nontransformed cells when those cells were aged ("very lumpy") when compared to yields observed in transformed cells. Berlin, et al., further disclose that addition of phytohormones to transformed suspensions did not enhance isoflavone production.

Cosio, et al., (1986; *J. Plant Physiol*, 124:155) disclose that thiarubrine synthesis by cells transformed by *Agrobacterium tumefaciens* is influenced by the degree of cellular organization rather than as a direct result of cellular transformation. Norton, et al., (1985; *Phytochemistry*, 24:719) discloses thiophene production in Tagetes cells transformed with *Agrobacterium tumefaciens* and concludes that it is not possible to predict the amounts of secondary metabolites produced as a result of transfers of genetic material from infected plants to crown galls and then to transformed callus tissues. Eilert, et al., (1987; *Plant Cell Reports*, 6:271) disclose that transformation of *Catharanthus roseus* cells with *Agrobacterium tumefaciens* did not enhance the accumulation of the alkaloid vindoline as compared to habituated, nontransformed cells. Additionally, transformed cells did not respond to elicitation with Pythium homogenate.

Tremouillaux-Guiller, et al., (1988; *Plant Cell Reports*, 7:456) examined alkaloid production in tissue cultures of *Choisya ternata*, and disclose that transformed cells showed lower production of balfourodinium in 21 transfrormed cell cultures compared to nontransformed cell cultures, and no difference in platydesminium between transformed and nontransformed lines.

It is known that *Agrobacterium rhizogenes* may be used to generate transformed root cultures. Transformed roots grow on hormone-free media and generally make the same secondary compounds found in nontransformed, differentiated root tissues (M. J. C. Rhodes, et al. (1990) IN: Charlwood, B. V. and M. J. C. Rhodes, Ed., *Secondary Products from Plant Tissue Culture*, Oxford University Press, New York).

Compounds referred to in the art as elicitors may be used to enhance the production of certain secondary metabolites. Elicitors may be biotic or abiotic compounds that stimulate a rapid increase in de novo synthesis of some plant secondary metabolites. Examples of elicitors include crude fungal extracts, metal ions, carbohydrates, and proteins (Chapter 11, pg. 333 IN: Payne, et al., *Plant Cell and Tissue Culture in Liquid Systems*, Oxford University Press, New York (1992). Repeated addition of elicitors to cell suspensions using a semi-continuous cultivation method is disclosed by Kurz (1987; IN: T. Mabry, Ed., *Plant Biotechnology Research Bottlenecks for Commercialization and Beyond*, IC$^2$ Institute, Austin, Tex.; Questions and strategies for productivity improvements). van der Heijden, et al., (1988; *Plant Cell Reports*, 7:51) disclose the use of elicitors to induce de novo synthesis of antimicrobial triterpenes in some Tabernaemontana species. The study focuses upon whether these antimicrobial triterpenes are phytoalexins. EP-A-0378921 (Crawford, et al.) discloses methods for monitoring the physiological state of cultured cells so that elicitors can be applied at an optimum time for enhancement of secondary metabolite production, that time being the end of the growth phase. The addition of cell viability stabilizers and/or nutrients at the time of elicitation is also disclosed.

Members of the family Melieae are known to contain bioactive compounds. In particular, compounds obtained from the neem tree, *Azadirachta indica* A. Juss (synonymous with *Melia azadirach*), are used in many products including soaps, toothpaste, cosmetics, pharmaceuticals, disinfectants, fertilizers, and insecticides (Jacobson M (1986), *Am. Chem. Soc. Symp. Ser.*, 296:220–232; Schmutterer, H. and K. R. S. Ascher (1987), Natural Pesticides from the Neem Tree (*Azadirachta indica* A. Juss) and other tropical plants: Proceedings of the 3rd International Neem Conference, Nairobi, Kenya 10–15 Jul., 1986, Deutsche Gesellschaft fur Technische Zusammenarbeit (GTZ) Eschborn Germany).

Azadirachtin, also referred to as neem, is an insecticidal tetranortriterpenoid present in *Azadirachta indica* A. Juss. Azadirachtin has insecticidal and antifeedant activities against a broad spectrum of insects (Schmutterer, H. and K. R. S. Ascher (1987) *Natural Pesticides from the Neem Tree* (*Azadirachta indica* A. Juss) and other *tropical plants : Proceedings of the* 3rd *International Neem Conference*, Nairobi, Kenya, 10–15 Jul., 1986, Deutsche Gesellschaft fur Technische Zusammenarbeit (GTZ) Eschborn, Germany; Jacobson, M., (1986) *Am. Chem. Soc. Symp. Ser.*, 296:220–232). Seeds are the primary source of azadirachtin for industrial scale production because they are the most concentrated source of azadirachtin, and they can most easily be harvested, transported, and extracted in large quantities.

*Azadirachta indica* has been introduced into cell culture in order to regenerate whole plants. Gautam, et al., (1991; In Vitro, 27(3): Pt 2:146A) disclose callus derived from anthers of *Azadirachta indica* and shoot organogenesis. Kokate, et al., (1989; In Vitro, 25(3) Pt 2 60A) disclose generation of callus from *Azadirachta indica* leaves for the study of electrokinetic potentials. Sanyal and Datta (1988; *Current Science*, India, 57 (1): 40–41) disclose generation of callus from tissues of *Azadirachta indica* to produce the triterpenoid nimbin. Sanyal and Datta disclose that nimbin gradually disappeared as cells dedifferentiated. Nimbin reappeared only after organogenesis. Naina, et al. (Current Science (1989) 58(4):184–187) disclose the regeneration of transformed whole plantlets from regions of *Azadirachta indica* seedlings infected with *Agrobacterium tumefaciens* strains K12×562E and K12×167. Naina, et al. disclose that *Azadirachta indica* offers great potential for agricultural, industrial and commercial exploitation as it is an excellent source of a variety of secondary metabolites. Naina, et al. point out that utilization of neem is limited by lack of knowledge about the tree and its specific climatic requirements. Schulz (Tissue Culture of *Azadirachta indica* IN: Schmutterer, H. and K. R. S. Ascher (1984) Natural Pesticides from the Neem Tree (*Azadirachta indica*, A. Juss) and other tropical plants: Deutsche Gesellschaft fur Technische Zusammenarbeit (GTZ) Eschborn, Germany) discloses tissue culture of *Azadirachta indica*. Callus formation and shoot organogenesis are described. Schulz reports that callus stopped growing after about six weeks in the presence of the phytohormones indole acetic acid and 2,4-dichlorophenoxyacetic acid (2,4-D). Although Shulz discloses the desirability of using tissue culture as a means for "biotechnical production of the insecticidal plant constituents" of *Azadirachta indica*. Schulz reports no specific disclosure of enhanced production of the insecticidally active substances.

It is important to realize that Azadirachta trees only grow in limited regions of the world. Seed production is therefore seasonal. However, an obstacle that has prevented the industrial-scale production of azadirachtin is establishing a reliable source of seeds containing adequate amounts of azadirachtin. Plant productivity and secondary metabolite content are influenced by the plant's environment, and season-to season variation in the azadirachtin content of seeds from the same geographical region may occur. Prior to collecting a large quantity of seed for extraction, it is important to measure the azadirachtin content of seeds to assure that the azadirachtin content is adequate for processing. In the subtropical regions where Azadirachta trees grow, the azadirachtin content of seeds may be substantially reduced if seeds are improperly stored or invaded by pathogens. Additionally, pathogens may produce toxic metabolites such as aflatoxin which may accumulate on seed surfaces and be extracted with azadirachtin during processing. Because Azadirachta seeds are available only seasonally, industrial processing is restricted to periods when seeds are available. The failure to identify sources of seeds of acceptable quality in any season can lead to disruptions in the manufacturing process.

In the case of azadirachtin and many other small molecules that are products of secondary metabolism, synthesis is achieved by complex, multienzyme pathways whose regulation is often not well understood. Because of the large number of enzymes involved, cloning of genes into microorganisms is not technically feasible. Up until now, the only routes to obtaining the desired product azadrachtin have been chemical synthesis and seed extraction. Chemical synthesis is too costly to be an economical source of azadirachtin. The disadvantages of seed extraction have already been described.

The present invention seeks to overcome the problems associated with the known processes.

BRIEF SUMMARY OF THE INVENTION

According to a first aspect of the present invention, there is provided a phytohormone-independent cell culture that is capable of producing bioactive compounds.

Preferably, the cell culture comprises cells from a member of the family Melieae, preferably *Azadirachta indica*.

According to a second aspect of the present invention, there is provided a phytohormone-independent cell culture of *Azadirachta indica* that is capable of producing bioactive compounds.

According to a third aspect of the present invention, there is provided azadirachtin free of contaminants from Azadirachta endocarps.

According to a fourth aspect of the present invention, there is provided a method for producing azadirachtin using cultured plant cells.

According to a fifth aspect of the present invention, there is provided a method for producing commercial-scale amounts of Azadirachta using suspension cultures from callus.

According to a sixth aspect of the present invention, there is provided a method for producing azadirachtin in aqueous solution, comprising inoculating sterile Azadirachta plant tissues with an oncogenic strain of *Agrobacterium tumefaciens*, removing the bacteria from the plant cells, generating callus cultures that grow on plant cell culture media in the absence of exogenously applied plant hormones, inoculating the callus cultures into liquid plant cell culture media (preferably phytohormone-free) to generate suspension cultures and harvesting azadirachtin secreted by the suspension cells from the culture media, optionally without killing the cells.

Preferably, the callus cultures are inoculated directly into the liquid plant cell culture media and not via an intermediate scale-up process.

Preferably, the Agrobacterium is the strain of *Agrobacterium tumefaciens* A281.

Preferably, one or more supplements selected from vitamins, carbohydrates, ions or phytohormones are added to the media.

Preferably, the cells are immobilized. Preferably, the cells are in beads; preferably beads are of calcium alginate.

Preferably, elicitors are added to the media at levels to increase azadirachtin production.

Preferably, the Azadirachtin is harvested using adsorbents.

Preferably, the azadirachtin is separated from other components and cell extracts by chromatographic techniques wherein a gradient of increasing concentration of acetonitrile in water, from about 20 percent to about 90 percent, is used.

The present invention therefore relates to the use of plant cell suspension culture of cells that yield bioactive compounds, such as azadirachtin-producing cells. The present invention overcomes the disadvantages of the known processes for the production of bioactive compounds, such as the isolation of azadirachtin by seed extraction. The aseptic culture of the present invention allows for the continuous production of azadirachtin that is free of pathogens and toxins, independent of environmental conditions, yields a predictable quantity and quality of bioactive product and permits continuous production at a desired, contained location. We recognized that plant cell culture presented a possible alternative to seed extraction for production of azadirachtin and other bioactive products. Known plant cell culture techniques could be used, such as those discussed in the literature, for example in Vasil, I, Ed. (1984) *Cell Culture and Somatic Cell Genetics of Plants*, Volume 1, Academic Press, New York; Charlwood, B. V. and M. J. C. Rhodes, Eds *Secondary Products from Plant Tissue Culture*, Oxford University Press, New York. One of the main advantages of plant cell culture is that it provides a process for predictable, consistent, year-round production of bioactive compounds that is independent of climate and free of pathogens and toxins.

The other advantages associated with the present invention are that it provides cells that produce useful bioactive compounds, it eliminates the known obstacles for the industrial production of useful bioactive products of *Azadirachta indica*, it provides a method for producing azadirachtin using cultured plant cells, it produces azadirachtin directly in aqueous solution, it provides a method for rapid production of commercial-scale Azadirachta suspension cultures from callus and it provides azadirachtin free of metabolites, including toxins, produced by pathogens that infest Azadirachta seeds.

DETAILED DESCRIPTION OF THE INVENTION

In one embodiment, the present invention involves the generation of *Azadirachta indica* cells in cell culture that produce the tetranortriterpenoid azadirachtin. It has been found that cells of *Azadirachta indica*, for example, leaf, hypocotyl or cotyledon cells, can be infected with oncogenic strains of *Agrobacterium tumefaciens* to produce callus cultures that grow on phytohormone-free media. Suspension-cultured cells of *Azadirachta indica* derived from those callus cultures secrete azadirachtin into the culture media. Azadirachtin secretion is preferred because it is not necessary to kill the cells to obtain azadirachtin. In brief, the process involves the steps of inoculating sterile plant tissues with an oncogenic strain of *Agrobacterium tumefaciens*, removing the bacteria from the plant cells, and generating callus cultures that grow on plant cell culture media in the absence of exogenously applied plant hormones. The callus cultures are inoculated into phytohormone-free liquid plant cell culture media to generate suspension cultures. Azadirachtin secreted by the suspension cells is harvested from the culture media without killing the cells. Cell viability may be maintained in culture over long periods of time, and the media from the same cell population may be repeatedly harvested to extract insecticidally-active azadirachtin.

In another embodiment of the present invention, and in order to obtain bioactive compounds from plant tissue culture, viable aseptic cell cultures are established. In order to achieve commercial levels of azadirachtin production, it is desired to produce cell suspension cultures that can be grown in bioreactors of appropriate scale to meet commercial production requirements, usually 10,000 to 20,000 liters. The first step in plant cell culture is generally to establish callus cultures. Various plant tissues may be used to establish cell cultures, for example, seeds (cotyledons, hypocotyls, embryos), leaves, meristems, stems, or roots. In a first step, tissue is surface-sterilized to kill microorganisms on tissue surfaces. Hypochlorite, chlorine dioxide or other surface-sterilizing agents known in the art may be used. Sterile leaf tissue may be obtained by surface-sterilizing seeds, germinating the seeds under aseptic conditions, then harvesting sterile tissues from the seedlings. Alternatively, leaf tissue from trees grown in a greenhouse or in the open environment may also be used. Leaf tissue grown under aseptic conditions is preferred because it is not necessary to supplement media with antibiotics to suppress the growth of diverse populations of microorganisms present on leaves grown in nonsterile environments.

It is preferred that phytohormone-independent callus cultures are generated by transformation of plant tissues with a competent oncogenic strain of *Agrobacterium tumefaciens*. Leaf tissue transformation is preferred, however, other tissues, such as seeds, roots, anthers, and hypocotyls may also be used. The hypervirulent strain of *Agrobacterium tumefaciens* A281 is the strain that is preferred for transformation, however, other oncogenic strains of *Agrobacterium tumefaciens* that are competent to infect Melieae may also be used. Sterile leaf sections are cut into two or more sections and inoculated by soaking in a dilute suspension of *Agrobacterium tumefaciens* (i.e., for one minute). The *Agrobacterium tumefaciens* is prepared by diluting an aliquot of a suspension culture of bacteria into sterile Murashige Skoog media lacking phytohormones. Leaf sections are removed from the *Agrobacterium tumefaciens* suspension, and any excess liquid is blotted off and placed on plant tissue culture media containing a gelling agent. Inoculation continues by incubating leaf sections for two to five days at 24 to 26 degrees centigrade. At the end of the inoculation time period, the tissues are transferred to a second media which contains one or more antibiotics which are toxic to Agrobacterium, but not to plant tissues, to kill viable Agrobacterium remaining in the culture. Suitable antibiotics for use in such a medium include cefotaxime and carbenicillin. After approximately three to five weeks, callus tissues may be observed at one or more sites on the infected leaf surfaces. As soon as discrete callus masses are large enough to excise with a scalpel, they may be cut away from the leaf surface and transferred to fresh hormone-free media.

The leaf and callus tissues are maintained on phytohormone-free media containing sufficient antibiotic to suppress bacterial growth until all bacterial cells are killed. Following eradication of the Agrobacterium, plant tissues may be maintained on phytohormone-free, antibiotic-free media. It is preferred that a number of independent callus lines be generated so that selection of lines with different levels of azadirachtin or (other bioactive compound) production may be identified.

In addition to callus tissues, transformed root cultures may be established by transformation of plant tissues using *Agrobacterium rhizogenes* (American Type Culture Collection (ATCC), Rockville, Md., strain 15834). Substantially the same transformation procedure is used for *A. rhizogenes* transformation as is used for *A. tumefaciens* transformation. Within two to four weeks after infection, hormone-independent roots may be excised from the leaf surface and transferred to fresh, hormone-free media. Optionally, callus and suspension cultures may also be derived from transformed roots by addition of appropriate phytohormones to induce dedifferentiation of transformed root tissues.

Although callus lines resulting from *A. tumefaciens* infection are preferred for azadirachtin production, clonal lines of nontransformed callus tissues may also be generated by placing surface-sterilized tissues, for example, leaves, seeds or stems, on a tissue culture media that induces callus cell growth. A suitable tissue culture media for induction and maintenance of callus is Murashige Skoog media supplemented with the phytohormones napthaleneacetic acid and benzyladenine each at between 0.1 and 2.0 milligrams per liter, and solidified with a gelling agent. Other formulations of salts and phytohormones may also be used to establish callus cultures. Additionally, antibacterial and antifungal agents may be added to the medium to maintain sterility. The callus generated may be unorganized and undifferentiated, or some degree of cellular organization or differentiation may occur.

The next step of establishing suspension cultures is accomplished by inoculating liquid media with callus cells. Suspension media may be identical in composition to the callus media except that in suspension media, no gelling agent is present.

The cellular material that is used to inoculate suspension cultures for scale-up of production processes is referred to as inoculum. It was surprisingly found that the transformed Azadirachta callus can be used directly as inoculum to initiate rapidly growing suspension cultures. Transformed callus is the preferred inoculum for beginning scale-up processes. Alternatively, the inoculum for large-scale production can be prepared by initiating a small scale suspension culture from callus or suspension cells, maintaining the culture as suspension for at least one serial transfer to fresh liquid culture media, and then using this suspension culture to inoculate the first of a series of increasingly larger culture vessels.

An advantage of initiating suspension cultures directly from callus is that such direct inoculation would substantially reduce the time required to achieve desired production cell volumes, thereby eliminating the time required to gradually increase cell numbers required for serial transfer using suspension cultures.

To enhance suspension cell growth, other media supplements, such as vitamins, carbohydrates, or phytohormones may optionally be added. Additionally, cells may be immobilized in beads of calcium alginate or other gelling agents, a technique known to those skilled in the art.

The productivity of suspension cell lines generated from transformed and nontransformed calli may be assessed by measuring extracellular azadirachtin in the suspension cell media that is secreted by suspension cells. Alternatively, azadirachtin may be measured by harvesting callus or suspension cells and extracting intracellular azadirachtin. Intracellular azadirachtin may be extracted by homogenizing cells in methanol or other solvent, such as acetonitrile or ethyl acetate. Methanol is preferred because of high extraction efficiency. At intervals of time after the callus or suspension culture is initiated, for example, every three days for thirty days, an aliquot of one or more cell cultures may be analyzed for azadirachtin content. Azadirachtin contents may be compared among different cell lines. The peak time of productivity may also be determined for each individual line.

High performance reverse-phase liquid chromatography may be used to analyze the concentration of azadirachtin in media or in cell extracts. To separate azadirachtin from other components, a gradient of increasing concentration of acetonitrile in water, from about 20 percent to about 90 percent, is preferred to achieve separation of azadirachtin from other components in media and in cell extracts. After the sample is applied to the chromatography column, the eluate is monitored at about 210 nanometers in the ultraviolet absorption spectrum. The elution pattern of an unknown mixture is compared to an elution pattern of authentic azadirachtin at a known concentration. A standard curve may be developed by chromatographic resolution and quantitation of several known concentrations of standard. Using the standard curve the concentration of azadirachtin in the unknown sample may be determined by linear regression. While reverse phase column chromatography is preferred, other methods of chromatographic separation may also be suitable for azadirachtin determination. Alternatively, azadirachtin may be detected by bioassay using insects susceptible to azadirachtin, for example, Mexican Bean Beetles (*Epilachna varivestis*). The mortality rate caused by exposure of the insects to the sample extract is compared to the mortality rate caused by authentic azadirachtin standard at a known concentration. Analytical methods such as mass spectrometry may be used to further confirm the identity of azadirachtin in the sample extracts.

Optionally, the azadirachtin in media or from cell extracts may be concentrated prior to analysis using chromatographic media such as resins in batch or column. It is preferred that the styrenic resin CG161 (TosoHaas Inc., Montgomeryville, Pa.) be used for azadirachtin concentration, however, other chromatographic media such as $C_{18}$ reverse phase resin may also be suitable. Azadirachtin in aqueous suspension binds to CG161, and contaminants are washed away using water, buffer or culture media. Azadirachtin is eluted from CG161 using solvent. The preferred solvent for azadirachtin elution is methanol, because azadirachtin is very soluble in methanol and may be quantitatively eluted from CG161 by methanol. The azadirachtin eluted from the resin may be directly analyzed by HPLC or by insect bioassay.

Production of azadirachtin in the suspension culture media may be enhanced by supplementing the suspension media with one or more phytohormones, for example, 2,4-dichlorophenoxyacetic acid (2,4-D), napthaleneacetic acid (NAA) and benzyladenine (BA) each at between one tenth and ten milligrams per liter. The effects of hormone addition may be additive. Other hormones alone or in combination may also be used.

Additionally, one or more elicitors may be added to the media to increase azadirachtin production compared with cells in media to which no elicitor is added. To enhance azadirachtin production, it is preferred that an autoclaved preparation of yeast extract at 1 to 40 milligrams per milliliter of media be added at least one time to the media. Extracts of killed Agrobacterium or killed fungi derived from Azadirachta seed coats are also effective elicitors. Additionally, other media amendments, such as phosphate starvation, phytohormones; ions, or other compounds may also be applied to enhance azadirachtin production.

The present invention will now be described by way of the following non-limiting procedures and examples.

PROCEDURE 1

Preparation of Standard Murashige Skoog Media and One-Half Strength Murashige Skoog Media Unless indicated otherwise, Murashige Skoog media was prepared by dissolving into one liter of glass distilled water: 1 package of Murashige Skoog basal salts (Gibco-BRL, Bethesda, Md.); 30 grams sucrose; 100 milligrams myo-inositol; 1 milliliter of 1000×B5 vitamin stock (nicotinic acid, 1 milligram per liter; thiamine-HCL, 10 milligrams per liter; pyridoxine-HCL, 1 milligram per liter). The media solution was adjusted to between pH 5.7 and 5.8. Nine grams of Difco Bacto Agar (Fisher Scientific, Pittsburg, Pa.) was added, and the suspension autoclaved at 250 degrees Farenheit, 15 PSI for 25 minutes. The media was poured into 100×20 millimeter plastic Petri Dishes (Fisher Scientific, Pittsburgh, Pa.) and allowed to solidify. When appropriate, filter-sterilized phytohormone solutions, prepared at 1 milligram per milliliter were added to molten media before pouring into plates.

One-half strength Murashige Skoog media was prepared by dissolving one package of Murashige Skoog basal salts and 15 grams of sucrose in two liters of glass distilled water. The solution was adjusted to between pH 5.7 and 5.8, and autoclaved using the conditions described above.

PROCEDURE 2.

Recovery of Azadirachtin from Cultured Cells and from Cell Culture Media

Azadirachtin was extracted from one to five grams of callus cells which were harvested from petri plates. The fresh weight of the harvested cells was recorded. Suspension cells were separated from media by centrifugation at 2,500×G for 5 minutes. The culture media was poured off, and cells were collected with a spatula. Excess liquid was blotted away using absorbent towels. The cell fresh weight was recorded. Callus or suspension cells were homogenized in methanol using a mortar and pestle. Approximately 1 to 5 milligrams of acid-washed sea sand (Fisher Scientific, Pittsburgh, Pa.) was added to the mortar to facilitate homogenization. Callus or suspension cells were extracted with methanol at the proportion of one milliliter of methanol per gram fresh weight of cells. The homogenates were poured into two milliliter microcentrifuge tubes and centrifuged for 15 minutes at 12,000 rpm (revolutions per minute) in a Jouan Model MR14.11 refrigerated microcentrifuge (Jouan Winchester, Va.). The supernatants were collected and their volumes were recorded. When media was to be analyzed, a three to five milliliter aliquot of media was drawn from the supernatant after centrifugation at 2,500×G for 5 minutes.

Azadirachtin in media or in cell extracts was concentrated by incubating two or three milliliters of media or extract with 500 microliters of a 1:1 (v:v resin:water) slurry of Amberchrom CG161 (TosoHaas, Montgomeryville, Pa.) for 30 minutes. The resin mixture was poured into a 12 milliliter PrepTorr™ column (Fisher Scientific, Pittsburg Pa.) and placed on a PrepTorr™ vacuum chamber. Excess aqueous media was removed from the resin by applying gentle vacuum. Azadirachtin was eluted from the resin by adding 500 microliters of methanol adjusted to pH 5.8, applying a vacuum to the column and collecting the eluate in a two milliliter microcentrifuge tube.

PROCEDURE 3

Quantitation of Azadirachtin by High Performance Liquid Chromatography (HPLC)

Azadirachtin in cultured plant tissues was measured by reverse phase high performance liquid chromatography. Extracts of callus, suspension cells, or cell culture media prepared as described above were applied to a Tosoh TSK-ODS120T $C_{18}$ reverse phase HPLC column (15 cm×4.6. mm; Thomson Instrument Company, Wilmington, Del.), equilibrated in 30 percent HPLC-grade acetonitrile in filtered, glass-distilled water. The high performance liquid chromatograph used was a TosoHaas Model TSK-6010 pump with a TosoHaas Model TSK-6041 ultraviolet detector (Thomson Instrument Co., Wilmington, Del.). Upon injection of the sample onto the column, a gradient of 30% to 60% acetonitrile was commenced and continued for twenty minutes at a flow rate of one milliliter per minute. The area under the peak eluting at the same retention time as authentic azadirachtin was recorded using a Hewlett Packard Model HP3396A integrator attached to the TSK-6010 pump. Authentic azadirachtin standards were purchased from Sigma Chemical Company (St. Louis, Mo.). Azadirachtin in the unknown samples was determined by linear regression, using a standard curve generated by running authentic azadirachtin in methanol of at least three concentrations under the same gradient conditions as the unknowns. The column was washed with 100% acetonitrile for five minutes following each sample run and then reequilibrated in 30% acetonitrile before beginning another sample run. The azadirachtin peak, under these running conditions, eluted at approximately 14.5 minutes after starting the gradient.

PROCEDURE 4

Insect Bioassay

Methanol extracts of callus and suspension cells were diluted to a concentration of 1 microgram per 62.5 microliters. To set up leaf disc assays, 47 millimeter circular adsorbent cellulose filter pads (Gelman Sciences, Ann Arbor, Mich.) were placed one per dish in 50×9 millimeter petri dishes. The filter paper discs were each moistened with 1 milliliter of sterile glass distilled water. Circular leaf discs (3 centimeters in diameter) were cut from fresh lima bean (*Phaseolus lunatus*) leaves, avoiding major veins. The leaf discs were placed adaxial surfaces down on the filter paper. One leaf disc was placed in each petri dish. Control and unknown azadirachtin samples were spread onto the entire area of the leaf surfaces, without damaging the leaf surfaces in the process. The extracts were allowed to evaporate to dryness. One Mexican Bean Beetle (second larval instar) was placed on each treated leaf disc and exposed to the sample extracts for three days. At three days, the filter paper and leaf disc in each plate was replaced with fresh, moistened filter paper and an untreated leaf disc. For each experiment, two control samples were used, one being no treatment to the leaf disc, and a second being 50 percent acetonitrile on the leaf disc. For each sample, ten replicate leaf discs were tested. The insects were observed at 1, 3, 6, 7 and 8 days and scored for mortality.

EXAMPLE 1

Establishing sterile plant cultures

Sterile trees were obtained by surface-sterilizing viable seeds within their endocarps for 30 minutes in a mixture of 20 milliliters of commercial bleach (Clorox (Procter and Gamble, Cincinatti, Ohio.) diluted to 100 milliliters with water. Then 0.01 milliliters Triton×100 (Sigma Chemical Company, St. Louis, Mo.) was added and the solution agitated to mix the components thoroughly. Fifty seeds were surface sterilized by agitating rapidly (200 rpm) for thirty minutes. The seeds were drained, then rinsed three times with sterile water for ten minutes per rinse. The last rinse was drained off of the seeds, and the wet seeds were allowed to sit overnight in aseptic conditions. The next day, the seeds were resterilized with Alcide LD disinfectant (Alcide Corporation, Norwalk, Conn.) for one and one half hours, with agitation at 200 rpm on a rotary platform shaker. The seeds were drained and used without further rinsing.

The endocarps (hardshells) were removed, using a scalpel and forceps, in a laminar flow hood under aseptic conditions. The seeds were placed in petri dishes containing one-half strength of Murashige Skoog media prepared as described in Procedure 1. The media was supplemented with 20 parts per million Dithane fungicide (Rohm and Haas Company, Philadelphia, Pa.), 50 parts per million Captan 50WP (ICI Americas, Inc., Wilmington, DE), and 250 milligrams per liter cefotaxime (Calbiochem, La Jolla, Calif.). The seeds were placed in an incubator set at 27 degrees centigrade, on a 16 hour light/8 hour dark cycle. During the approximately two weeks required for germination, uncontaminated seeds were transferred to fresh plates when any seeds on a plate became contaminated. At the end of two to four weeks, sterile germinated seedlings were transferred to Magenta boxes (Sigma, St. Louis, Mo.) containing one-half Murashige Skoog salts without fungicides or antibiotics, and returned to the incubator.

EXAMPLE 2

Generation of Hormone-Independent Callus Cultures

Sterile leaves were cut under aseptic conditions from plants described in Example 1 and incubated for one minute in a suspension of *Agrobacterium tumefaciens* A281. *A. tumefaciens* was prepared by inoculating 50 milliliters of Luria broth (10 grams per liter bacto tryprone, 5 grams per liter sodium chloride, 5 grams per liter yeast extract, pH 7.0) and incubating overnight in a rotary shaker at 250 rpm, 30 degrees C. A dilute suspension ($OD_{600}$=0.05) of Agrobacterium was prepared in sterile Murashige Skoog salts, pH 5.7. Leaf pieces were cut into sections approximately 1×2 cm, wounded slightly on their surfaces by pinching with forceps, to increase the number of potential infection sites. The leaf pieces were incubated for one minute in the Agrobacterium suspension, touched on one edge to sterile filter paper to remove excess liquid, and placed on hormone-free Murashige Skoog media. After an incubation at 28 degrees C. in the dark for 48 hours, leaf pieces were transferred to hormone-free Murashige Skoog media supplemented with 250 milligrams per milliliter cefotaxime, and incubated at 28 degrees C. with a 16 hour light/8 hour dark cycle. After approximately two weeks, callus appeared around wound sites. When the callus was of sufficient size to remove from the leaf surface, individual callus masses were subcultured on fresh plates containing the same media. Cefotaxime was maintained in the media for at least six subcultures, then omitted from the media. If bacterial growth was observed after removal of cefotaxime, callus was transferred to fresh plates of hormone-free media supplemented with 250 milligrams per liter of cefotaxime and maintained on the antibiotic until no further bacterial growth was observed. Callus was transferred to fresh media every four to six weeks and maintained under the same culture conditions. Azadirachtin was extracted from cells and from culture media using Procedure 2. Azadirachtin was analyzed by HPLC using Procedure 3.

EXAMPLE 3

Generation of Hormone-Independent Suspension Cell Cultures

Rapidly growing callus maintained on hormone-free Murashige Skoog media was inoculated into 125 milliliter Erlenmeyer flasks containing 30 milliliters of standard Murashige Skoog media (Procedure 1) lacking agar. Callus was inoculated at one to one and one half grams per 30 milliliters of media. Cultures were incubated at room temperature, which fluctuated between 25 and 30 degrees C., shaken at 110 rpm on a New Brunswick incubator shaker (Model G10 gyrotory shaker; New Brunswick, Edison, N.J.). for three to four weeks, at which time a thick suspension was obtained (approximately two to three grams per 30 milliliters, depending upon the cell line being tested). Data are presented in Table 1.

TABLE 1

Azadirachtin (for suspension cell culture media, micrograms per milliliter of media; for suspension cell culture cells, micrograms per milliliter of extract)

| Cell Line | Sample | Culture time in Days | | | | | |
|---|---|---|---|---|---|---|---|
| | | 10 | 15 | 17 | 21 | 24 | 27 |
| A281/118 | cells | nd | — | 0.03 | — | nd | — |
| A281/118 | media | nd | — | 0.06 | — | 0.10 | — |
| A281/125 | cells | 0.14 | — | nd | — | nd | — |
| A281/125 | media | 0.31 | — | 0.06 | — | 0.10 | — |
| A281/130 | cells | 0.19 | — | 0.60 | — | 0.32 | — |
| A281/130 | media | 0.32 | — | 0.11 | — | 0.16 | — |
| A281/135 | cells | 0.12 | — | 0.08 | — | 0.34 | — |
| A281/135 | media | 0.09 | — | 0.12 | — | 0.04 | — |
| A281/167 | cells | — | nd | — | 0.65 | — | 0.23 |
| A281/167 | media | — | 0.04 | — | 0.63 | — | 0.49 | nd — not detected;
— not analyzed

EXAMPLE 4

Generation of Hormone-Dependent Callus

Sterile leaves, cotyledons and hypocotyls of Example 1 were placed on Murashige Skoog media supplemented with 1 milligram per liter napthaleneacetic acid and 1 milligram per liter benzyladenine. Tissues were incubated for three to six weeks at 28 degrees C., 16 hours light/8 hours dark. When individual callus masses could be excised, they were subcultured onto fresh media of the same composition and maintained under the same culture conditions. Calli were subcultured every four to six weeks.

EXAMPLE 5

Generation of Transformed Root Cultures

Sterile leaves of Example 1 were infected with *Agrobacterium rhizogenes* (-ATCC 15834). *A. rhizogenes* was prepared by inoculating 50 milliliters of Luria broth (10 grams per liter bacto tryptone, 5 grams per liter sodium chloride, 5 grams per liter yeast extract, pH 7.0) and incubating overnight in a rotary shaker at 250 rpm, 30 degrees C. A dilute suspension ($OD_{600}$=0.05) of Agrobacterium was prepared in sterile Murashige Skoog salts, pH 5.7. Leaf pieces were cut into sections approximately 1×2 cm, wounded slightly on their surfaces by pinching with forceps, to increase the number of potential infection sites. The leaf pieces were incubated for one minute in the Agrobacterium suspension, touched on one edge to sterile filter paper to remove excess liquid, and placed on hormone-free Murashige Skoog media. After an incubation at 28 degrees C. in the dark for 48 hours, leaf pieces were transferred to standard Murashige Skoog media supplemented with 250 milligrams per milliliter cefotaxime, and incubated at 28 degrees C. with a 16 hour light/8 hour dark cycle. After approximately two weeks, roots appeared at original wound sites. When the roots were of sufficient size to remove from the leaf surface, individual roots were excised, then subcultured on fresh plates containing the same media. Cefotaxime was maintained in the media for at least six subcultures, then omitted from the media. If bacterial growth was observed after removal of cefotaxime, roots were transferred to fresh plates of hormone-free media supplemented with 250 milligrams per liter of cefotaxime and maintained on the antibiotic until no further bacterial growth was observed. Roots were transferred to fresh media every four to six weeks and maintained under the same culture conditions. Representative concentrations of azadirachtin extracted from root cultures are presented in Table 2.

TABLE 2

| Root Line | Azadirachtin Micrograms per gram fresh weight |
|---|---|
| RKA-1 | 0.60 |
| RKA-2 | 1.68 |
| RKA-3 | 0.29 |
| R201 | 0.42 |

EXAMPLE 6

Enhancing Azadirachtin Production Using Biotic Elicitors

Suspension cells of Example 3 were grown 10 days in Murashige Skoog media. At 10 days, an elicitor was added to the culture media at the final concentration indicated in Table 3. Agrobacterium elicitor was prepared by growing Agrobacterium tumefaciens A281 in (media) overnight at 28 degrees C. at 250 rpm on a rotary shaker. The stationary phase culture was autoclaved for 15 minutes at 120 degrees C., 43.9×10$^{-4}$ kgm$^2$(15 psi) to kill bacterial cells. The autoclaved extract was centrifuged at 10,000 rpm for 10 minutes to remove cell debris, and the supernatant was used for elicitor studies. An unidentified fungus isolated from the coats of azadirachtin seeds was cultured for 5 days in potato dextrose broth, then autoclaved and centrifuged using the same conditions as used for preparation of the Agrobacterium elicitor. At the time of elicitor addition, $CaCl_2$ (2.5 mm final concentration) and glycerol (1% (v/v) final concentration) were also added to the culture media. The samples were incubated for 24 hours under standard conditions of 25 to 27 degrees C., shaken at 110 rpm on a rotary platform shaker. A 5 milliliter sample of suspension media was collected at 24 hour intervals for 96 hours. After each sampling, the cultures were returned to standard conditions. The media was sampled by HPLC using Procedure 3. Results are presented in Table 3.

TABLE 3

| | | (Azadirachtin in media) (micrograms per milliliter) Hours after addition of elicitor to media | | | | |
|---|---|---|---|---|---|---|
| Cell Line | Elicitor | Elicitor Concentration | 0 | 24 | 48 | 72 | 144 |
| A281/135 | yeast | 10 mg/ml | nd | nd | 0.78 | 0.06 | nd |
| A281/135 | Agrobacterium | .16 ml/ml | nd | nd | nd | nd | 0.07 |
| A281/135 | seed fungus | .16 ml/ml | nd | nd | nd | 1.10 | nd |
| A281/146 | yeast | 10 mg/ml | nd | nd | 0.41 | 0.80 | 0.49 |
| A281/146 | Agrobacterium | .16 ml/ml | nd | 0.14 | 0.10 | 0.85 | nd |
| A281/146 | seed fungus | .16 ml/ml | nd | nd | 0.10 | nd | nd |
| A281/167 | yeast | 10 mg/ml | nd | 1.37 | 0.71 | 0.18 | 0.17 |
| A281/167 | Agrobacterium | .16 ml/ml | nd | 0.12 | 0.45 | 0.92 | 0.09 |
| A281/167 | seed fungus | .16 ml/ml | nd | 0.28 | 0.28 | 0.43 | 0.25 | nd — not detected

EXAMPLE 7

Repeated Elicitation of Suspension Cells to Enhance Azadirachtin Production

A $2^{5-1}$ fractional factorial experiment was designed to compare the effects on two different cell lines of repeated addition of 5 or 10 milligrams per milliliter of yeast elicitor, presence of phosphate in the medium, and presence of 2,4-D (1-milligram per liter) in the media. For this experiment, media were made according to the following recipe and adjusted to a final pH of 5.7 to 5.8:

TABLE 4

| Murashige Skoog Media with and without phosphate salt | |
|---|---|
| Constituent | milligrams per liter |
| ammonium nitrate | 1650 |
| potassium nitrate | 1900 |
| magnesium sulfate heptahydrate | 370 |
| potassium phosphate, monobasic | 170 |
| ferric EDTA | 43 |
| sucrose | 30,000 |
| calcium chloride dihydrate | 440 |
| potassium iodide | 0.83 |
| boric acid | 620 |
| manganese sulfate tetrahydrate | 2230 |
| zinc sulfate heptahydrate | 860 |
| sodium molybdate dihydrate | 25 |
| copper sulfate pentahydrate | 2.5 |
| cobalt chloride hexahydrate | 2.5 |
| nicotinic acid | 1.0 |
| thiamine HCl | 10.0 |
| pyridoxine HCl | 1.0 |
| myo-inositol | 100 |

For this example, two versions of the media were prepared; one as described and the other as a phosphate-free media (omitting the 170 milligrams of monobasic potassium phosphate). Suspension cultures from two independent cell lines (A281/124 and A281/135) were initiated by inoculating transformed callus from Example 2 (30 g of A281/135 and 40 grams of A281/124) into 300 milliliters of Murashige Skoog media with phosphate as described in Table 4. Cells were inoculated into one liter erlenmeyer baffle flasks (Bellco Glass, Vineland, N.J.) and incubated under standard conditions of 28 degrees C. for 14 days on a rotary shaker platform set at 110 rpm. The following processes were carried out separately for each cell line. The suspension culture was sieved through a two millimeter stainless steel mesh (Fisher Scientific, Pittsburgh, Pa.). Cells and aggregates of less than 2 millimeters were collected and combined into a single flask. The cells were centrifuged at 2,500×G for 5 minutes, the media was poured off. Twenty grams of A281/135 and 50 grams of A281/124 cells were placed into a clean sterile flask containing 240 milliliters of fresh Murashige Skoog media (Table 4, with phosphate). Differences in amounts of cell aggregation account for the differences in fresh cell weights. Line A281/124 did not aggregate into clumps of more than 2 mm, whereas the proportion of clumps exceeding 2 mm in A281/135 made up a larger percentage of the culture. The samples were aged for 4 days. In a next step, a sequential halving procedure was used to prepare eight flasks of the same cell density. The flask containing 240 milliliters of sieved cells was swirled and the contents split equally between two new sterile flasks. The cells in these two flasks were each swirled and each split into two equal portions to generate four flasks with equal cell densities and media volumes. This sequential halving process was continued until eight flasks containing 30 milliliters of media in 125 milliliter flasks were generated for each of the two cell lines.

The contents of individual flasks were poured into a 50 milliliter sterile polypropylene centrifuge tube, capped and centrifuged for 5 minutes at 2,500×G to pellet the cells. The media was poured off, and the fresh weight of each sample was measured using aseptic conditions. The cells were returned to clean 125 ml flasks and the media was replaced with 30 milliliters of Murashige Skoog media either with or without phosphate, according to Table 5. The suspension cultures were incubated for three days under standard conditions to deplete appropriate cultures of phosphate. On the fourth day, designated 0 (zero) hours of the experiment, the cultures were poured into sterile 50 milliliter centrifuge tubes, centrifuged for five minutes at 2,500×G, and the fresh weight of each sample was recorded. A 3 milliliter sample of the media was saved and prepared according to Procedure 2 for HPLC analysis using Procedure 3. The cells were returned to the flasks, and the media was replaced with the appropriate amendments of elicitor, phosphate and hormone as listed in Table 5.

The suspensions were incubated for twenty four hours under standard conditions. At 24 hours, the cells were harvested by centrifugation at 2,500×G for 5 minutes, and a three milliliter sample of the media was collected for HPLC analysis. The remainder of the media was discarded. The cells were returned to the flasks, and the media was replaced with media containing the appropriate amendments as indicated in Table 5. The procedure was repeated at 48, 72 and 96 hours. Samples which were not repeatedly elicited did not receive any elicitor after the original addition at zero hours. For samples that were repeatedly elicited, elicitor at the appropriate level was added a zero, 24, 48, and 72 hours. All samples were stored at minus 20 degrees C. until the end of the experiment and all were processed according to Procedure 3 at the same time in an order designated by the experimental design to reduce sampling bias. The results are presented in Table 5.

TABLE 5

| Sample Number | Cell Line | Repeat Elicitation | Phosphate Present | Mg/ml Elicitor | 2,4-D present | Azadirachtin in media (mg/ml) Hours after addition of elicitor | | | |
|---|---|---|---|---|---|---|---|---|---|
| | | | | | | 24 | 48 | 72 | 96 |
| 1 | A281/135 | No | No | 5 | Yes | 0.09 | 8.89 | nd | 0.08 |
| 2 | A281/124 | No | No | 5 | No | 0.08 | 10.32 | .19 | nd |
| 3 | A281/135 | Yes | No | 5 | No | 0.09 | 0.11 | 0.12 | 0.15 |
| 4 | A281/124 | Yes | No | 5 | Yes | 0.12 | 0.12 | 0.13 | 0.13 |
| 5 | A281/135 | No | Yes | 5 | No | nd | 10.65 | 0.12 | 0.13 |
| 6 | A281/124 | No | Yes | 5 | Yes | 0.13 | 0.10 | nd | nd |
| 7 | A281/135 | Yes | Yes | 5 | Yes | 0.09 | 0.08 | 0.14 | 0.14 |
| 8 | A281/124 | Yes | Yes | 5 | No | nd | 0.20 | 0.18 | nd |
| 9 | A281/135 | No | No | 10 | No | 0.01 | 0.16 | nd | nd |
| 10 | A281/124 | No | No | 10 | Yes | nd | 8.16 | nd | nd |
| 11 | A281/135 | Yes | No | 10 | Yes | nd | 1.04 | 0.13 | nd |
| 12 | A281/124 | Yes | No | 10 | No | 0.06 | 1.72 | 0.23 | 0.43 |
| 13 | A281/135 | No | Yes | 10 | Yes | nd | 2.23 | 0.12 | 0.13 |
| 14 | A281/124 | No | Yes | 10 | No | nd | 0.34 | nd | 0.34 |
| 15 | A281/135 | Yes | Yes | 10 | No | nd | 9.91 | 0.17 | nd |
| 16 | A281/124 | Yes | Yes | 10 | Yes | nd | nd | 0.13 | nd | nd — not detected

EXAMPLE 8

Repeated Elicitation of Suspension Cell Cultures to Enhance Azadirachtin Production Thirty grams of callus cells of cell line A281/135 were inoculated in 400 milliliters of standard Murashige Skoog media in a one liter baffle flask, and incubated under standard conditions for three weeks. At three weeks, the cell suspension was filtered through a sterile two millimeter mesh into a 1 liter baffle flask containing 240 milliliters of Murashige Skoog media. The suspension was aged for 24 hours, then the culture was centrifuged at 2,500×G for 5 minutes. Eight grams of cells were placed in 120 milliliters of minimal Murashige Skoog media (Table 4) media (media lacking phosphate). A sequential splitting procedure was used to divide these cells into four equal 30 milliliter aliquots in 125 milliliter flasks. Similarly, eight grams of cells were placed into 120 milliliters of complete Murashige Skoog media (with phosphate, Table 4). A sequential splitting procedure was used to divide these cells into four equal 30 milliliter aliquots in 125 milliliter flasks. The samples were aged for 5 days under standard conditions to deplete cells in media lacking phosphate of intracellular phosphate. On the fifth day, designated hour 0 (zero), of the experiment, 2,4-D at 1 milligram per liter, or yeast elicitor at either 5 or 10 milligrams per milliliter were added according to Table 6 and returned to the standard incubation conditions.

At 24 hours, 3 milliliter media samples were removed from each flask. The samples that did not receive repeated elicitation were not further treated. Samples 1 and 6, which received repeated elicitation, were treated as follows: the suspension were poured into centrifuge tubes, centrifuged at 2,500×G for 5 minutes, and the media was discarded. New media containing elicitor at the same level was added to the cells, which were returned to the 125 milliliter flask, then incubated under standard conditions. Media samples (3 milliliters) were removed from each sample at 48 and 72 hours with no further media changes to any samples. Media samples were prepared for HPLC as in Procedure 3, after all samples had been collected. Prior to sample preparation, all samples were stored at minus 20° C. Azadirachtin production in the samples are presented in Table 6.

TABLE 6

| Sample No. | Elicitation repeated | Phosphate present | Elicitor Level | 2,4-d Present | Azadirachtin in media (micrograms/milliliter) Hours after elicitor added | | |
|---|---|---|---|---|---|---|---|
| | | | | | 24 | 48 | 72 |
| 1 | yes | no | 5 | no | 0.17 | 11.11 | 10.91 |
| 2 | no | no | 10 | no | 0.24 | 13.33 | 14.70 |
| 3 | no | no | 5 | no | 0.11 | 0.15 | 0.14 |
| 4 | no | no | 10 | yes | 3.75 | 14.70 | 17.81 |
| 5 | no | yes | 5 | no | 0.14 | 9.78 | 12.34 |
| 6 | yes | yes | 5 | yes | 0.44 | 6.57 | 6.42 |
| 7 | no | yes | 10 | yes | 0.99 | 5.15 | 15.54 |
| 8 | no | yes | 10 | no | 021 | 12.93 | 16.27 |

EXAMPLE 9

Insect Bioassay of Media Samples from Elicitor-Treated Suspension Cell Cultures

Media samples collected from selected samples of Example 8 were bioassayed to test for biological activity against Mexican Bean Beetles according to Procedure 4. Extracts of culture media were applied to lima bean leaves. By eight days, all insects fed extracts of cell suspension media were either dead or moribund, while 11 out of 12 insects on control leaf discs were alive at 8 days. Results of the assay are presented in Table 7.

EXAMPLE 10

Mass Spectroscopic Detection of Azadirachtin in Cultured Azadirachta Cells

Extracts obtained from three independent suspension cultures generated according to Example 3 were analyzed by mass spectroscopy for the presence of authentic azadirachtin. The samples analyzed were single peak fractions obtained by chromatographic separation of whole cell extracts using the high performance liquid chromatography method described in Procedure 3. For each sample, the peak eluting at a retention time of approximately 14.5 minutes, and at an acetonitrile: water mixture of approximately 45:55 was collected and evaporated to dryness in an air stream of room temperature air. The dry extract was redissolved in 10 microliters of methanol, and one microliter of this solution was placed on the mass spectrometer desorption chemical probe filament.

The analysis was performed on a Jeol HX-110 (Tokyo, Japan) mass spectrometer using the following conditions. The source was operated in the desorption chemical ionization (DCI) mode at approximately 40 degrees centigrade with isobutane as reagent gas at a source housing pressure of $2.2 \times 10^{-6}$ torr. The filament was heated at 1 ampere/minute, and the ionizing electron current was set at 50 microamperes at an energy of 200 electron volts. At a mass resolving power of 1000 the magnetic field was scanned from a mass to charge ratio (m/z) 650 to 750 with a one second cycle time. The one microliter of a 300 nanogram per microliter azadirachtin standard was used to check the performance of the instrument. The diagnostic peaks of the authentic standard were the protonated molecular ion at m/z 721 and the peak at m/z 703 due to the loss of water. The relative abundance of the peak at m/z 703 was generally two to three times that of the peak at m/z 721. Analysis of cell lines A281/130, A281/131, and A281/135, each having a peak eluting at approximately 14.5 minutes and 45 percent acetonitile using HPLC, were all found to contain the peaks diagnostic for azadirachtin. [Note: The use of freeze-drying should be avoided in sample preparation; it was observed to result in loss of azadirachtin from commercial standard and samples].

EXAMPLE 11

Use of Resinous,Adsorbents to Enhance Azadirachtin Production

The removal of accumulated product with resinous adsorbents was used to enhance the production of azadirachtin by

TABLE 7

| Sample Number. | Elicitation repeated | Phosphate present | Elicitor level | 2,4-D present | Insect Condition at 8 Days | | |
|---|---|---|---|---|---|---|---|
| | | | | | Live | Dead | Moribund |
| no treatment control | no | no | none | no | 6 | 0 | 0 |
| acetonitrile control | no | no | none | no | 5 | 1 | 0 |
| 1 | yes | no | 5 | no | 0 | 7 | 3 |
| 2 | no | no | 10 | yes | 0 | 8 | 2 |
| 3 | no | no | 5 | no | 0 | 8 | 2 |
| 4 | no | no | 10 | yes | 0 | 8 | 2 |
| 5 | no | yes | 10 | no | 0 | 5 | 5 |
| 6 | no | yes | 10 | yes | 0 | 6 | 4 | suspension cell cultures. A281/124 and A281/135 suspension cultures were incubated with sterilized non-functionalized, macroporous acrylate based polymeric absorbent (sold under the trademark Ambersorb® XAD-7 absorbent, hereinafter ("XAD-7 absorbent") or non-functionalized, macroporous styrenic-based polymeric absorbent (sold under the trademark Ambersorb® XAD-16 absorbent, hereinafter ("XAD-16 absorbent") added directly to the suspension media. The resins were washed extensively with distilled water prior to use. Interstitial water was removed from the resin immediately before weighing by plating resin on several layers of clean filter paper. 1.48 g to 1.52 g of the appropriate resin was weighed directly into a tared 250 ml erlenmeyer flask. Five milliliters of basal media was added to each flask prior to autoclaving at 250 degrees Farenheit, 15 PSI (pounds per square inch) for 20 minutes. Control flasks contained 5 ml of basal MSA media. These flasks were capped and sterilized by autoclaving.

Suspension cultures were initiated by inoculating one gram of callus of cell lines A281/124 or A281/135 into 30 ml of basal MS media in 125 ml erlenmeyer flasks. The cultures were incubated for 14 days at 27° C., 100 RPM in a Queue controlled-temperature incubator-shaker at which time the suspension cells and media were poured into preweighed sterile 50 ml certrifuge tubes and centrifuged at 2,500×G for 5 minutes to gently pellet suspension cells to separate them from the conditioned media. The conditioned media was poured out of the tubes and back into the original culture flask. Cell fresh weight for each sample was determined by weighing the cells in the preweighed 50 ml centrifuge tubes and subtracting the weights of the tubes. The cells and conditioned media from which they were originally separated were recombined and added to flasks containing 5 ml of basal media containing XAD-7 absorbent or XAD-16 absorbent, or no resin, and returned to the incubator-shaker to incubate at 27° C., 100 RPM for 4 to 10 days. On each harvest day, triplicate samples of the cells and resin, or cells without resin (controls) were transferred to preweighed 50 ml centrifuge tubes, the cells and resin were pelleted. Ten to 15 ml of media was collected for analysis and the rest of the media was discarded. Cells and resin were weighed to determine fresh weight and then were frozen at −20° C. until analysis. Analysis was begun by thawing cells plus resin, placing them in plastic 250 ml bottles, and adding methanol at a ratio of approximately 1:1 cell weight:methanol volume. The bottles were tightly capped and placed on a gyratory shaker for 7 days to extract the azadirachtin. The cells and resin beads were homogenized together using a mortar and pestle. The homogenates were poured into two milliliter microcentrifuge tubes and centrifuged for 15 minutes at 12,000 rpm (revolutions per minute) in a Jouan Model MR14.11 refrigerated microcentrifuge (Jouan Winchester, Va.). The supernatants were collected and their volumes recorded. When media was to be analyzed, a three to five milliliter aliquot of media was drawn from the supernatant after centrifugation at 2,500×G for 5 minutes. The samples were either measured directly without concentration by HPLC analysis according to Procedure 3, or azadirachtin in media or cell extracts. Azadirachtin in media or in cell extracts was concentrated by incubating two or three milliliters of media or extract with 500 microliter of 1:1 (v:v) resin;water) slurry of Amberchrom CG161 (TosoHaas, Montgomeryville, Pa.) for 30 minutes. The resin mixture was poured into a 12 milliliter Prep Torr™ column (Fisher Scientific, Pittsburgh, Pa.) and placed on a Prep Torr™ vacuum chamber. Excess aqueous media was removed from the resin by applying gentle vacuum. Azadirachtin was eluted from the resin by adding 500 microliters of methanol adjusted to pH5.8, applying a vacuum to the column and collecting the eluate in a two milliliter microcentrifuge tube.

The cell and resin samples were homogenized using a mortar and pestle and extracted according to the method of Procedure 2 before HPLC analysis according to the method of Procedure 3. Several media samples from cultures incubated in the presence of resin were selected at random and analyzed by HPLC according to the method or Procedure 3. No azadirachtin was detected in any media samples. Azadirachtin production was enhanced in the presence of XAD-7 absorbent and XAD-16 absorbent as shown in Table 8.

TABLE 8

Experiment to test effect of addition of XAD-7 and XAD-16 adsorbents on azadirachtin production in cultured Azadirachta suspension cells. Sterile resin was added directly to cultures and the analyses reflect the sum of azadirachtin in the cells and adsorbed onto the resin.

| Line # | Day of Harvest | Resin | Azadirachtin µ/g fresh wt (cels and resin) |
|---|---|---|---|
| A281/135 | 0 | none | n.d.[1] |
| A281/135 | 4 | none | 0.50 (0.50)[2] |
| A281/135 | 4 | XAD-7 | 17.07 (4.63) |
| A281/135 | 4 | XAD-16 | 5.48 (1.31) |
| A281/135 | 10 | none | n.d. |
| A281/135 | 10 | XAD-7 | 1.48 (.265) |
| A281/135 | 10 | XAD-16 | 22.5 (4.63) |
| A281/124 | 0 | none | 2.42 (.35) |
| A281/124 | 4 | none | 0.57 (0.81) |
| A281/124 | 4 | XAD-7 | 57.83 (1.90) |
| A281/124 | 4 | XAD-16 | 27.55 (8.9) |
| A281/124 | 10 | none | 0.62 (.88) |
| A281/124 | 10 | XAD-7 | 40.58 (4.22) |
| A281/124 | 10 | XAD-16 | 32.19 (16.0) |

[1] n.d. not detected
[2] expressed as mean (standard deviation)

We claim:

1. A method for producing azadirachtin, comprising:
   a) introducing genes coding for phytohormones into *Azadirachta indica* cells by infecting the cells with a competent oncogenic strain of *Agrobacterium tumefaciens*;
   b) killing the *Agrobacterium tumefaciens* with at least one antibiotic which is toxic to the Agrobacterium but not to the Azadirachta cells;
   c) culturing the cells from step b) on phytohormone-free media until callus masses form;
   d) excising one or more callus masses and transferring the masses to phytohormone-free media;
   e) inoculating a liquid suspension media with callus cells from the callus masses of step d);
   f) culturing the callus cells in the liquid suspension media to produce azadirachtin, and
   g) recovering the azadirachtin.

2. The method of claim 1 wherein the *Agrobacterium tumefaciens* is *Agrobacterium tumefaciens* A281.

3. The method of claim 1 further comprising after step f) and before step g) a step of separating the cells from the liquid suspension media forming a cell portion and a liquid suspension media portion.

4. The method of claim 3 wherein the azadirachtin is recovered from the liquid suspension media portion.

5. The method of claim 3 wherein the azadirachtin is recovered from the cell portion.

* * * * *